US009119538B2

(12) United States Patent
Uesaka et al.

(10) Patent No.: US 9,119,538 B2
(45) Date of Patent: Sep. 1, 2015

(54) ELECTRONIC SPHYGMOMANOMETER

(71) Applicants: Chisato Uesaka, Kyoto (JP); Yukiya Sawanoi, Nara (JP); Hiroyuki Kinoshita, Kyoto (JP)

(72) Inventors: Chisato Uesaka, Kyoto (JP); Yukiya Sawanoi, Nara (JP); Hiroyuki Kinoshita, Kyoto (JP)

(73) Assignee: OMRON HEALTHCARE Co., Ltd., Kyoto (JP)

(*) Notice: Subject to any disclaimer, the term of this patent is extended or adjusted under 35 U.S.C. 154(b) by 456 days.

(21) Appl. No.: 13/720,147

(22) Filed: Dec. 19, 2012

(65) Prior Publication Data
US 2013/0109981 A1 May 2, 2013

Related U.S. Application Data

(63) Continuation of application No. PCT/JP2011/064286, filed on Jun. 22, 2011.

(30) Foreign Application Priority Data

Jul. 21, 2010 (JP) .................................. 2010-163942

(51) Int. Cl.
*A61B 5/0225* (2006.01)
*A61B 5/022* (2006.01)
*A61B 5/0235* (2006.01)
*A61B 5/00* (2006.01)

(52) U.S. Cl.
CPC ............. *A61B 5/0225* (2013.01); *A61B 5/0235* (2013.01); *A61B 5/02233* (2013.01); *A61B 5/6824* (2013.01)

(58) Field of Classification Search
CPC ..... A61B 5/021; A61B 5/022; A61B 5/02208; A61B 5/02216; A61B 5/02225; A61B 5/02233; A61B 5/02241; A61B 5/0225; A61B 5/02255; A61B 5/023; A61B 5/0235
See application file for complete search history.

(56) References Cited

U.S. PATENT DOCUMENTS 7,611,468 B2 * 11/2009 Inoue et al. .................... 600/490
8,308,648 B2 * 11/2012 Sano et al. ..................... 600/493

(Continued)

FOREIGN PATENT DOCUMENTS

JP 3149873 B2 3/2001
JP 2005-230175 A 9/2005

(Continued)

OTHER PUBLICATIONS

International Search Report issued in corresponding International Application No. PCT/JP2011/064286 dated Jul. 19, 2011, and English translation thereof (4 pages).

(Continued)

*Primary Examiner* — Navin Natnithithadha
*Assistant Examiner* — Meredith Weare
(74) *Attorney, Agent, or Firm* — Osha Liang LLP

(57) ABSTRACT

A CPU of a sphygmomanometer includes a first control unit that, during measurement, controls a change in the internal pressure of a measurement air bladder by controlling the driving of a pump and/or a valve. The CPU further includes a second control unit that controls a change in the internal pressure of a compressing air bladder by controlling the driving of a pump and/or a valve. During measurement, the second control unit carries out control so that the internal pressure of the compressing air bladder is a predetermined ratio to the internal pressure of the measurement air bladder controlled by the first control unit.

12 Claims, 12 Drawing Sheets

(56) References Cited

U.S. PATENT DOCUMENTS

| | | |
|---|---|---|
| 8,622,917 B2 * | 1/2014 | Eto et al. .................. 600/490 |
| 8,808,189 B2 * | 8/2014 | Tokko et al. ................ 600/490 |
| 2005/0182332 A1 | 8/2005 | Sano et al. |
| 2005/0234350 A1 | 10/2005 | Sawanoi et al. |
| 2005/0240109 A1 * | 10/2005 | Inoue et al. ................ 600/499 |
| 2009/0312651 A1 * | 12/2009 | Sano et al. ................ 600/493 |
| 2010/0268092 A1 | 10/2010 | Kobayashi et al. |
| 2011/0251499 A1 * | 10/2011 | Eto et al. .................. 600/490 |
| 2011/0257540 A1 * | 10/2011 | Sawanoi et al. ............ 600/494 |
| 2011/0295130 A1 * | 12/2011 | Tokko et al. ............... 600/494 |
| 2013/0030310 A1 * | 1/2013 | Sawanoi et al. ............ 600/494 |

FOREIGN PATENT DOCUMENTS

| | | |
|---|---|---|
| JP | 2005-304670 A | 11/2005 |
| JP | 2007-167171 A | 7/2007 |
| JP | 2009-119067 A | 6/2009 |
| JP | 2009-279196 A | 12/2009 |
| JP | 2010-142418 A | 7/2010 |
| WO | 2010/071052 A1 | 6/2010 |

OTHER PUBLICATIONS

Patent Abstracts of Japan, Publication No. 2005-230175, Published on Sep. 2, 2005, 1 page.
Patent Abstracts of Japan, Publication No. 2009-279196, Published on Dec. 3, 2009, 1 page.
Patent Abstracts of Japan, Publication No. 2007-167171, Published on Jul. 5, 2007, 1 page.
Patent Abstracts of Japan, Publication No. 2005-304670, Published on Nov. 4, 2005, 1 page.
Patent Abstracts of Japan, Publication No. 2010-142418, Published on Jul. 1, 2010, 1 page.
Patent Abstracts of Japan, Publication No. 2009-119067, Published on Jun. 4, 2009, 1 page.

* cited by examiner

CIRCUMFERENTIAL LENGTH [cm]

BLOOD PRESSURE VALUE [mmHg]

| PREDETERMINED RATIO [%] | | SYSTOLIC BLOOD PRESSURE VALUE (mmHg) | | | |
|---|---|---|---|---|---|
| | | ~100 | 100~140 | 140~180 | 180~ |
| CIRCUMFERENTIAL LENGTH (cm) | 17~22 | 117 | 113 | 107 | 105 |
| | 22~32 | 120 | 115 | 110 | 108 |
| | 32~42 | 136 | 128 | 125 | 123 |

ELECTRONIC SPHYGMOMANOMETER

TECHNICAL FIELD

This invention relates to electronic sphygmomanometers, and particularly relates to electronic sphygmomanometers that automatically wrap a measurement band (a cuff) containing an air bladder around a measurement area.

BACKGROUND ART

Blood pressure is one index for analyzing cardiovascular disease, and performing a risk analysis based on blood pressure is effective in preventing cardiovascular-related conditions such as stroke, heart failure, and myocardial infarction.

Thus far, diagnoses have been made using blood pressure (casual blood pressure) measured at medical institutions, such as during hospital visits, health checkups, and so on. However, recent research has shown that blood pressure measured at home (home blood pressure) is more useful in diagnosing cardiovascular disease than casual blood pressure. As a result, sphygmomanometers for use at home are becoming widespread.

Many household sphygmomanometers employ an oscillometric or microphone blood pressure measurement technique. In oscillometric blood pressure measurement, a measurement band (cuff) that contains an air bladder is wrapped around a measurement area such as an upper arm, the internal pressure of the cuff (a cuff pressure) is increased to a predetermined pressure (for example, 30 mmHg) beyond the systolic blood pressure, and a change in the volume of the artery is detected as a change in the pressure overlapping the cuff pressure (a pressure pulse wave amplitude) while the cuff pressure is reduced gradually or in steps; the systolic blood pressure and the diastolic blood pressure are determined based on the changes in the pressure pulse wave amplitude. Furthermore, with the oscillometric technique, it is possible to measure blood pressure by detecting a pressure pulse wave amplitude occurring while the cuff pressure is being increased.

Meanwhile, in the microphone technique, the cuff is wrapped around a measurement area such as the upper arm and the cuff pressure is increased to a predetermined pressure beyond the systolic blood pressure, in the same manner as with the oscillometric technique. Thereafter, the Korotkoff sound produced by the artery is detected by a microphone provided within the cuff as the cuff pressure is gradually reduced; the cuff pressure when the Korotkoff sound is produced is taken as the systolic blood pressure, whereas the cuff pressure when the Korotkoff sound is weak or is not present is taken as the diastolic blood pressure.

With either method, if the cuff of the sphygmomanometer is not properly wrapped around the measurement area, the cuff pressure will not be sufficiently transmitted to the artery, resulting in a drop in the measurement accuracy. Accordingly, with respect to a sphygmomanometer having a configuration that automatically wraps a cuff around a measurement area (called a "fully-automatic arm sphygmomanometer" hereinafter), the present applicants have, in JP 2005-230175A (Patent Literature 1), previously disclosed a technique in which a curler configured of a flexible member and a wrapping air bladder are disposed on the outside of a measurement air bladder for wrapping the measurement air bladder around the measurement area; by inflating the wrapping air bladder, the diameter of the curler is reduced, thus wrapping the measurement air bladder around the measurement area.

Furthermore, the present applicants have, in JP 2009-279196A (Patent Literature 2), previously disclosed a technique for improving the accuracy of oscillometric blood pressure measurement; with this technique, the measurement accuracy is improved by reducing skew in a detected pressure pulse wave amplitude through control that brings an air exhaust flow amount from a measurement air bladder per unit of time into a proportional relationship with a speed of deflation of the measurement air bladder.

SUMMARY OF INVENTION

Incidentally, the cuff structure in a fully-automatic arm sphygmomanometer is a dual structure, including a measurement air bladder that to carry out blood pressure measurement compresses an artery in a measurement area, detects a change in the volume of the artery occurring as the pressure is gradually increased or decreased as a change in the pressure within the air bladder, and calculates a blood pressure based on that pressure change as described earlier, as well as a wrapping mechanism for wrapping the measurement air bladder around the measurement area. The flexible member ("curler", hereinafter) is provided between these two structures.

With the fully-automatic arm sphygmomanometer, the wrapping air bladder is inflated by supplying air thereto and the measurement air bladder is wrapped around the measurement area using the curler; after this, the pressure pulse wave amplitude is detected while inflating/deflating the measurement air bladder, and the systolic blood pressure and diastolic blood pressure are determined based on changes in the pressure pulse wave amplitude.

Accordingly, with this measurement method, the curler will expand outward in the radial direction in the case where the pressure of the wrapping mechanism is lower than the pressure of the measurement air bladder, whereas the curler will constrict inward in the radial direction in the case where the pressure of the wrapping mechanism is greater than the pressure of the measurement air bladder. Accordingly, the measurement air bladder will not properly pressurize the measurement area, and the pressure pulse wave amplitude cannot be correctly detected. In addition, when the curler has moved inward or outward in the radial direction in this manner, a false pulse wave may be produced by the resulting vibrations, which can influence the measurement accuracy.

Therefore, one or more embodiments of the present invention provide, particularly in an electronic sphygmomanometer that automatically wraps a measurement band (cuff) containing an air bladder around a measurement area, an electronic sphygmomanometer that controls a measurement air bladder pressure and a wrapping mechanism pressure so that the cuff is properly wrapped around the measurement area.

According to one or more embodiments of the present invention, an electronic sphygmomanometer includes a first fluid bladder, a first adjustment unit for injecting/exhausting a fluid into/from the first fluid bladder at a variable speed, a sensor for detecting an internal pressure of the first fluid bladder, a wrapping unit for wrapping the first fluid bladder around a measurement area of a measurement subject at a variable wrapping strength, a second adjustment unit for adjusting the wrapping strength of the wrapping unit, and a control unit. The control unit executes a first control process that outputs a first control signal to the first adjustment unit so that a rate of change in the internal pressure and/or fluid amount in the first fluid bladder becomes a predetermined rate of change, a second control process that outputs a second control signal to the second adjustment unit so that the wrapping strength reaches a predetermined ratio with the rate of change in the internal pressure and/or fluid amount in the first fluid bladder under the first control process, and a calculation process that calculates a blood pressure value of the measurement subject based on a change in the internal pressure of the first fluid bladder detected under the first control process.

According to one or more embodiments of the present invention, the first control signal is set in advance so that the rate of change in the internal pressure in the first fluid bladder and the rate of change in the fluid amount in the first fluid bladder are in a proportional relationship, the second control signal is set in advance in according with the first control signal so as to achieve the predetermined ratio, and the control unit carries out feed-forward control on the first control process and the second control process.

According to one or more embodiments of the present invention, the wrapping unit includes a second fluid bladder that is located further from the measurement area than the first fluid bladder when worn on the measurement area, the second adjustment unit includes a pump for injecting and/or a value for exhausting the fluid into/from the second fluid bladder at a variable speed, and the second control process includes a process for determining a driving voltage for the pump and/or the valve.

According to one or more embodiments of the present invention, the control unit sets the predetermined ratio to a pre-set ratio or changes the predetermined ratio using a pre-set compensation formula in accordance with at least one of a circumferential length of the measurement area, an already-measured blood pressure value of the measurement subject, a blood pressure value of the measurement subject maintained during inflation, a size of the first fluid bladder, and a maximum value of the pressure in the first fluid bladder.

According to one or more embodiments of the present invention, the control unit determines the circumferential length of the measurement area and/or the size of the first fluid bladder based on a rate of change in the internal pressure of the first fluid bladder during inflation.

According to one or more embodiments of the present invention, the control unit determines the blood pressure value of the measurement subject by obtaining a previous measurement result.

According to one or more embodiments of the present invention, in the calculation process, the control unit calculates the blood pressure value based on a change in the internal pressure in the first fluid bladder when the first fluid bladder is deflating under the first control process, and the control unit takes the blood pressure value calculated based on a change in the internal pressure in the first fluid bladder when the first fluid bladder is inflating as a blood pressure value of the measurement subject used to determine the predetermined ratio.

According to one or more embodiments of the present invention, the electronic sphygmomanometer further includes an input unit for accepting an input of the at least one of a circumferential length of the measurement area, the already-measured blood pressure value of the measurement subject, a size of the first fluid bladder, and a maximum value of the pressure in the first fluid bladder.

According to one or more embodiments of the present invention, the electronic sphygmomanometer further includes a readout unit for reading out, from another device, the at least one of a circumferential length of the measurement area, the already-measured blood pressure value of the measurement subject, a size of the first fluid bladder, and a maximum value of the pressure in the first fluid bladder.

According to one or more embodiments of the present invention, the control unit changes the predetermined ratio to a pre-set ratio or changes the predetermined ratio using a pre-set compensation formula at at least one of a time when the internal pressure of the first fluid bladder reaches a predetermined level, a time when the wrapping strength reaches a predetermined level, and a time when a predetermined amount of time has elapsed following a predetermined point in time of a measurement process.

According to one or more embodiments of the present invention, the control unit changes the predetermined ratio to a pre-set ratio or changes the predetermined ratio using a pre-set compensation formula in accordance with a size of a pulse wave amplitude detected from the internal pressure of the first fluid bladder.

A control method according to one or more embodiments of the present invention is a control method for an electronic sphygmomanometer that has a first fluid bladder, a first adjustment unit for injecting/exhausting a fluid into/from the first fluid bladder at a variable speed, a sensor for detecting an internal pressure of the first fluid bladder, and a wrapping unit for wrapping the first fluid bladder around a measurement area of a measurement subject at a variable wrapping strength, the control method including a step of controlling the first adjustment unit so that a rate of change in the internal pressure and/or fluid amount in the first fluid bladder becomes a predetermined rate of change, a step of controlling a second adjustment unit so that the wrapping strength reaches a predetermined ratio with the rate of change in the internal pressure and/or fluid amount in the first fluid bladder under the control in the step of controlling the first adjustment unit, and a step of calculating a blood pressure value of the measurement subject based on a change in the internal pressure of the first fluid bladder detected under the control of the step of controlling the first adjustment unit.

According to one or more embodiments of the present invention, a cuff can be properly wrapped around a measurement area during measurement, and thus the measurement accuracy can be improved.

DETAILED DESCRIPTION OF INVENTION

Figure 1:
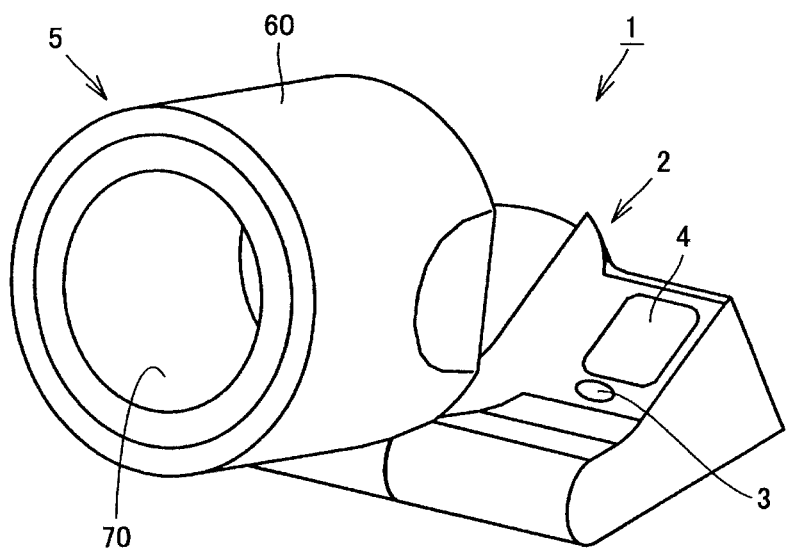
FIG. 1 is a perspective view illustrating a specific example of an external view of a sphygmomanometer according to a first embodiment.

Hereinafter, embodiments of the present invention will be described with reference to the drawings. In the following descriptions, identical reference numerals are added to identical components or constituent elements. The names and functions thereof are also the same.

First Embodiment

Apparatus Configuration

FIG. 1 is a perspective view illustrating a specific example of an external view of a blood pressure measurement apparatus (called a "sphygmomanometer" hereinafter) 1 according to a first embodiment.

As shown in FIG. 1, the sphygmomanometer 1 according to the present embodiment primarily includes a main body 2 that is placed on a desk or the like and a measurement section 5 into which an upper arm serving as a measurement area is inserted. An operating unit 3, in which a power switch, a measurement switch, a stop switch, a user selection switch, and the like are disposed, a display unit 4, and an elbow rest are provided in a top portion of the main body 2. Meanwhile, the measurement section 5 is attached so that the angle thereof relative to the main body 2 can be varied, and includes a housing 60 that is a casing having an approximately cylindrical shape, as well as a body compression/stabilizing unit contained in an inner circumferential area of the housing 60. Note that as shown in FIG. 1, in a normal usage state, the body compression/stabilizing unit contained in the inner circumferential area of the housing 60 is not exposed, and is covered by a cover 70.

Figure 2:
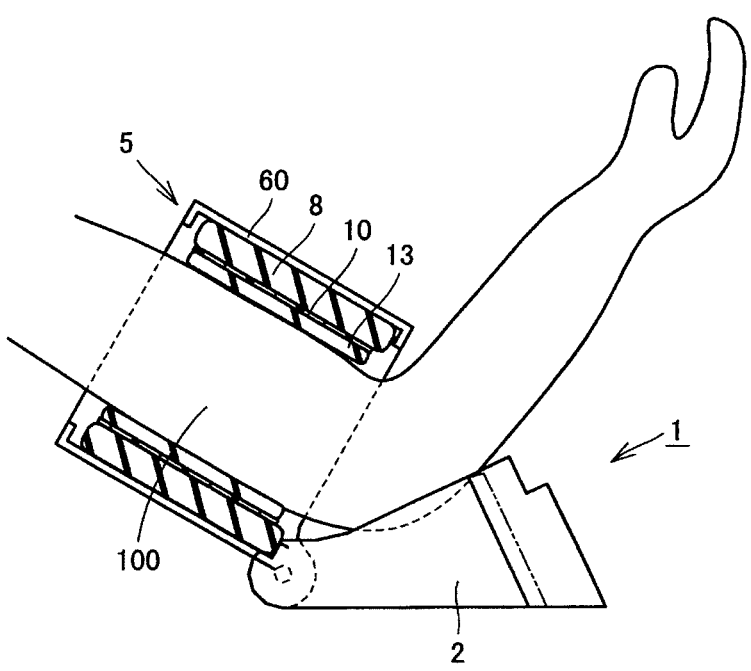
FIG. 2 is a cross-sectional schematic diagram illustrating the sphygmomanometer during blood pressure measurement.

FIG. 2 is a cross-sectional schematic diagram illustrating the sphygmomanometer 1 during blood pressure measurement. As shown in FIG. 2, during blood pressure measurement, an upper arm 100 is inserted into the housing 60, the elbow is placed on the stated elbow rest, and the measurement is instructed to start. The upper arm 100 is compressed and stabilized by the stated body compression/stabilizing unit, and the blood pressure is measured.

The body compression/stabilizing unit includes: an air bladder 13 that corresponds to a cuff and serves as a measurement fluid bladder for compressing the measurement area and measuring the blood pressure; a curler 10 that is located on the outside of the air bladder 13 and serves as an approximately cylindrical flexible member capable of expanding and contracting in the radial direction; and an air bladder 8, positioned on the outside of the curler 10, serving as a fluid bladder that causes the curler 10 to contract by expanding and compressing an outer circumferential surface of the curler 10 in the inward direction, that stabilizes the air bladder 13 against the measurement area of a body by pressing the air bladder 13 thereagainst over the curler 10 and the housing.

Figure 3:
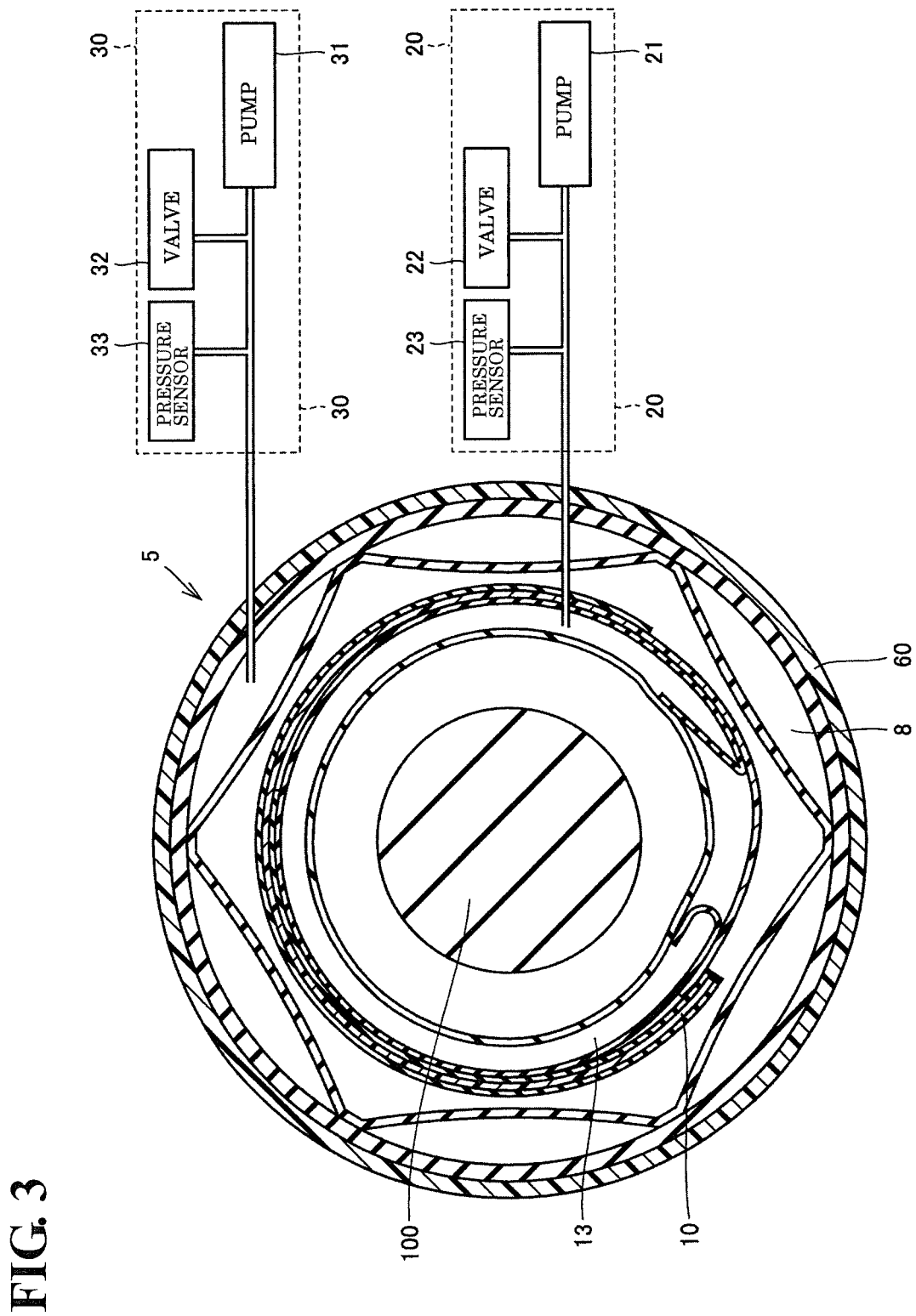
FIG. 3 is a cross-sectional view illustrating the internal structure of a measurement section.

FIG. 3 is a cross-sectional view illustrating the internal structure of the measurement section 5. As shown in FIG. 3, in the measurement section 5, the air bladder 8 is provided on the inner side of the housing 60, and expands/contracts using a compression and stabilization air system 30 (see FIG. 4), which will be mentioned later.

The curler 10, which is configured of a plate-shaped member that has been wrapped into an approximately cylindrical shape, is disposed on the inner side of the air bladder 8 (that is, the side toward the measurement area), and elastically deforms in the radial direction when an external force is applied thereto. The air bladder 13 is provided on the inner side of the curler 10, and expands/contracts using a measurement air system 20 (see FIG. 4), which will be mentioned later.

Figure 4:
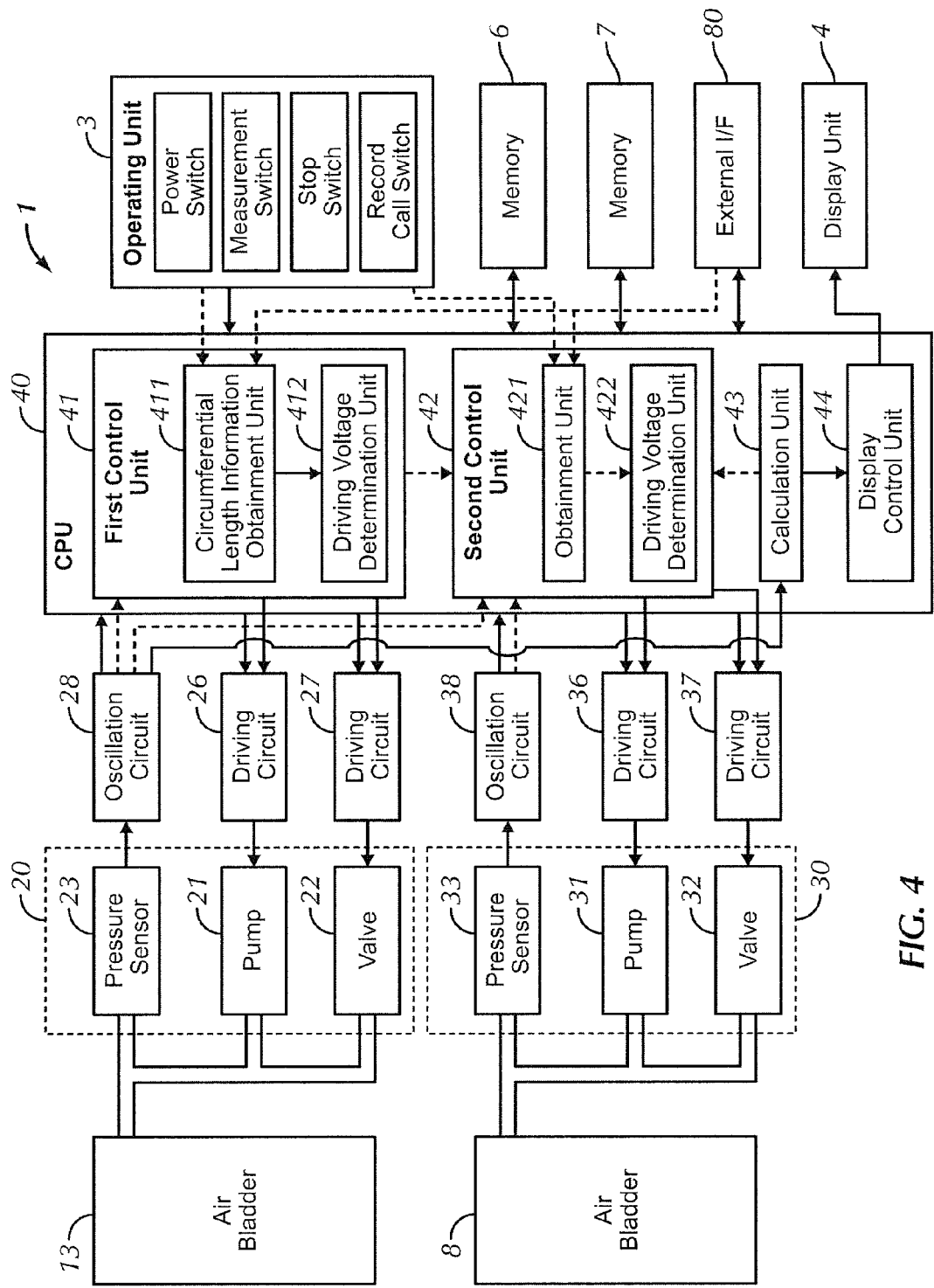
FIG. 4 is a block diagram illustrating a specific example of the functional configuration of the sphygmomanometer.

FIG. 4 is a block diagram illustrating a specific example of the functional configuration of the sphygmomanometer 1.

As shown in FIG. 4, the sphygmomanometer 1 includes the air bladder 13 and the air bladder 8, which are connected to the measurement air system 20 and the compression and stabilization air system 30, respectively. The air system 20 includes a pressure sensor 23 for measuring an internal pressure of the air bladder 13, a pump 21 for supplying/exhausting air to/from the air bladder 13, and a valve 22, whereas the air system 30 includes a pressure sensor 33 for measuring an internal pressure of the air bladder 8, a pump 31 for supplying/exhausting air to/from the air bladder 8, and a valve 32.

The air bladder 13 is connected to the pressure sensor 23 for measuring changes in the internal pressure of the air bladder 13, the pump 21 for injecting/exhausting air into/from the air bladder 13, and the valve 22. The air bladder 8 is connected to the pressure sensor 33 for measuring changes in the internal pressure of the air bladder 8, the pump 31 for injecting/exhausting air into/from the air bladder 8, and the valve 32.

The pressure sensors 23 and 33, the pumps 21 and 31, and the valves 22 and 32 are respectively connected to oscillation circuits 28 and 38, driving circuits 26 and 36, and driving circuits 27 and 37; meanwhile, the oscillation circuits 28 and 38, the driving circuits 26 and 36, and the driving circuits 27 and 37 are all connected to a CPU (central processing unit) 40 for controlling the sphygmomanometer 1 as a whole.

Furthermore, the display unit 4, the operating unit 3, a memory 6 that stores programs executed by the CPU 40 and serves as a work area when executing programs, a memory 7 that stores measurement results and the like, and an external interface (I/F) 80 for connecting to an external device and outputting/inputting data, are connected to the CPU 40.

The CPU 40 includes: a first control unit 41 for controlling the pump 21 and the valve 22 by outputting control signals to the driving circuits 26 and 27; a second control unit 42 for controlling the pump 31 and the valve 32 by outputting control signals to the driving circuits 36 and 37; a calculation unit 43 for calculating a blood pressure value based on a pressure signal from the pressure sensor 23; and a display control unit 44 for carrying out control for displaying measurement results and the like in the display unit 4. These are implemented in the CPU 40 by the CPU 40 executing predetermined programs stored in the memory 6 based on operation signals inputted from the operating unit 3.

The driving circuits 26 and 36 drive the pumps 21 and 31, respectively, in accordance with control signals from the CPU 40. As a result, air is injected into the air bladders 13 and 8.

The driving circuits 27 and 37 drive the valves 22 and 32, respectively, in accordance with control signals from the CPU 40. As a result, the valves 22 and 32 are opened/closed. Furthermore, the opening widths thereof (called a "gap" hereinafter) are controlled as well, thus controlling the exhaust amount and the exhaust speed of the air in the air bladders 13 and 8.

The pressure sensors 23 and 33 are electrostatic capacitance-type pressure sensors, and capacity values thereof change as the internal pressures of the air bladders 13 and 8 change. The pressure sensors 23 and 33 are connected to the oscillation circuits 28 and 38, respectively, and the oscillation circuits 28 and 38 convert the capacity values of the pressure sensors 23 and 33 into oscillation frequency signals based thereon and input those signals into the CPU 40.

The first control unit 41 and the second control unit 42 of the CPU 40 control the pumps 21 and 31 and the valves 22 and 32 by outputting control signals to the driving circuits 26 and 27 and the driving circuits 36 and 37. Meanwhile, the calculation unit 43 of the CPU 40 calculates a blood pressure value based on changes in the internal pressure of the air bladder 13 obtained from the pressure sensor 23. The display control unit 44 of the CPU 40 carries out a process for displaying a measurement result in the display unit 4, and outputs data and a control signal for carrying out the display to the display unit 4. Furthermore, the CPU 40 carries out a process for storing the blood pressure value in the memory 7.

Measurement Operation

Figure 5:
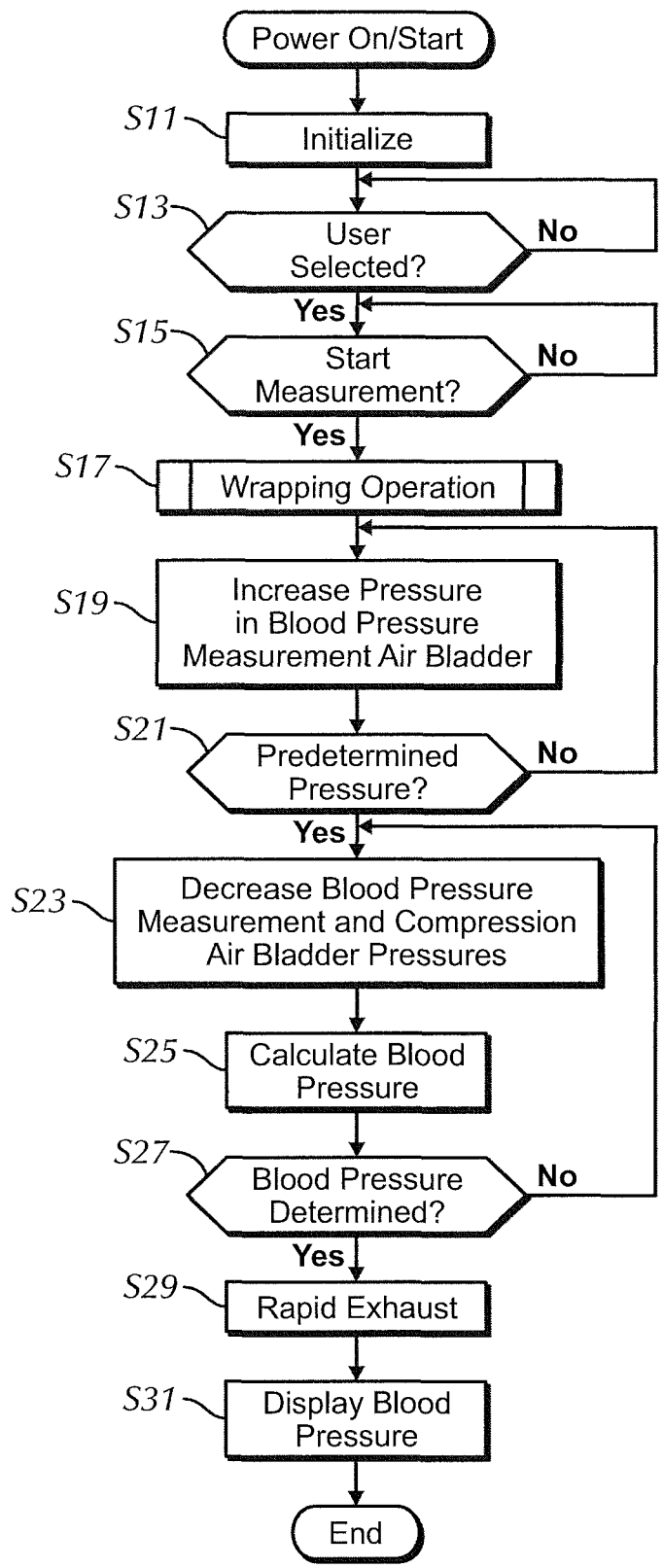
FIG. 5 is a flowchart illustrating a blood pressure measurement operation performed by the sphygmomanometer according to the first embodiment.

FIG. 5 is a flowchart illustrating a blood pressure measurement operation performed by the sphygmomanometer 1 according to the first embodiment. The blood pressure measurement operation illustrated in the flowchart in FIG. 5 is an operation carried out in the case where the CPU 40 calculates a blood pressure value based on changes in the internal pressure of the air bladder 13 as the air bladder 13 is deflating. This operation is commenced when the CPU 40 receives an operation signal as a result of the power switch in the operating unit 3 being depressed, and is implemented by the CPU 40 reading out a program stored in the memory 6 and controlling the various units illustrated in FIG. 4.

As shown in FIG. 5, after initialization has first been executed in step S11, the CPU 40 stands by until the user selection switch and the measurement switch have been depressed.

Next, when the CPU 40 receives an operation signal resulting from the user selection switch being depressed, and then receives an operation signal resulting from the measurement switch being depressed (YES in step S13 and YES in step S15), in step S17, the CPU 40 commences a wrapping operation, which is an operation for properly wrapping the air bladder 13 around an upper arm of the user, which serves as the measurement area.

Operations such as those described hereinafter can be given as example of the operations carried out here. That is, after the CPU has inflated the air bladder 13 in a preparatory manner by supplying a predetermined amount of air thereto, the CPU 40 inflates the air bladder 8 until the internal pressure of the air bladder 13 and changes in the internal pressure thereof reach predetermined values that have been set in advance. The measurement air bladder 13 is properly wrapped around the upper arm of the user, which serves as the measurement area, in an automatic manner through this operation.

Next, in step S19, the CPU 40 executes an inflation operation for increasing the internal pressure of the measurement air bladder 13 to a predetermined internal pressure. During this operation, the CPU 40 monitors the internal pressure of the air bladder 13 obtained from the pressure sensor 23, and determines whether or not a predetermined pressure set in advance has been reached. The "predetermined pressure" referred to here may be a pressure high enough to close off a blood vessel. Alternatively, in the case where a measurement result from the selected user is stored in the memory 7, the predetermined pressure may be a pressure obtained by adding a predetermined value to the systolic blood pressure value of that user.

When it is determined that the internal pressure of the air bladder 13 has reached the aforementioned predetermined pressure (YES in step S21), the CPU 40 executes, in step S23, a deflation operation for starting the deflation of the air bladders 13 and 8. The deflation operation is continued until a blood pressure calculation (S25), which will be mentioned later, is complete.

In step S25, the CPU 40 calculates a blood pressure value based on changes in the internal pressure of the air bladder 13 during the operation for deflating the air bladder 13 carried out in step S23. When the blood pressure value calculation is complete and a blood pressure value has been determined (YES in step S27), the CPU 40 ends the deflation operation of step S23, quickly reduces the internal pressures of the air bladders 13 and 8 in step S29, and releases the compression on the body. Then, in step S31, the CPU 40 executes an operation for displaying the calculated blood pressure value in the display unit 4 as a measurement result.

This ends the series of operations.

Internal Pressure Control of Air Bladder 13

(1) Feedback Control

In the aforementioned deflation operation of step S23, the first control unit 41 of the CPU 40 may monitor the internal pressure and changes in the internal pressure of the air bladder 13 and carry out feedback control that controls the rate of change in the internal pressure so that those values reach predetermined values.

In this case, as shown in FIG. 4, the first control unit 41 of the CPU 40 includes a driving voltage determination unit 412 for determining a voltage for driving the pump 21, the valve 22, and so on (called a "driving voltage E1" hereinafter).

The driving voltage determination unit 412 obtains the internal pressure and changes in the internal pressure of the air bladder 13, and determines the driving voltage E1 so as to establish a change rate in the internal pressure so that those values reach predetermined values. A control signal for driving the pump 21 and/or the valve 22 at the determined driving voltage E1 is generated, and the control signal is outputted to the driving circuit 26 and/or the driving circuit 27.

(2) Feed-Forward Control

Alternatively, in the aforementioned deflation operation of step S23, the first control unit 41 of the CPU 40 may carry out feed-forward control that controls the internal pressure and changes in the internal pressure of the air bladder 13 by outputting a control signal that has been set in advance. A case in which feed-forward control is carried out will now be described in detail.

In this case, as shown in FIG. 4, the first control unit 41 of the CPU 40 includes a circumferential length information obtainment unit 411 for obtaining circumferential length information that is information indicating the circumferential length of the measurement area of the user, and the driving voltage determination unit 412 for determining the driving voltage E1 for driving the valve 22.

When circumferential length information indicating, for example, "wide", "narrow", or the like is inputted during measurement using, for example, a switch of which the operating unit 3 is partially configured, the circumferential length information obtainment unit 411 obtains the circumferential length information based on an operation signal from the operating unit 3. Alternatively, the circumferential length information may be obtained through an input from the external I/F 80.

Further still, internal pressure control for obtaining the circumferential length information may be carried out by the CPU 40, and the circumferential length information obtainment unit 411 may obtain the circumferential length information based on the result of that control. Specifically, after accepting the selection of a user in the aforementioned measurement operations, the CPU 40 outputs, to the driving circuit 26, a control signal for driving the pump 21 at a predetermined voltage that is specified in advance, and inflates the air bladder 13 by driving the pump 21 at the predetermined voltage until the air bladder 13 reaches a predetermined pressure that is specified in advance. The CPU 40 measures the amount of time required until the predetermined pressure is reached. The circumferential length information obtainment unit 411 stores a correspondence relationship between the amount of time required until the predetermined pressure is reached and the circumferential length, and can obtain the circumferential length information of the user based on that correspondence relationship.

Here, in the case where the driving voltage for driving the pump 21 is the same, the inflation speed decreases as the circumferential length of the measurement area increases. Accordingly, the amount of time required for the inflation increases as the circumferential length of the measurement area increases. In other words, the inflation time required for the air bladder 13 to reach the predetermined pressure can be taken as an index that indicates the circumferential length of the measurement area. Accordingly, by storing, in advance, correspondence relationships in which the circumferential length is greater the longer the amount of time required for the inflation is, the circumferential length information obtainment unit 411 can obtain the circumferential length based on the amount of time required for the inflation. Note that this information can be obtained in the same manner from the rotational frequency of the pump 21 and the pressure in the air bladder 13, instead of the inflation time.

Alternatively, as another example, a cloth (not shown) serving as a mechanism for wrapping the air bladder 13 around the measurement area has slide resistance, and the circumferential length information obtainment unit 411 may obtain the circumferential length information from a resistance value obtained from the stated slide resistance when the air bladder 13 is wrapped around the measurement area.

The driving voltage determination unit 412 determines the driving voltage E1 based on the obtained circumferential length information. The determination of the driving voltage E1 by the driving voltage determination unit 412 will be described hereinafter.

Figure 6:
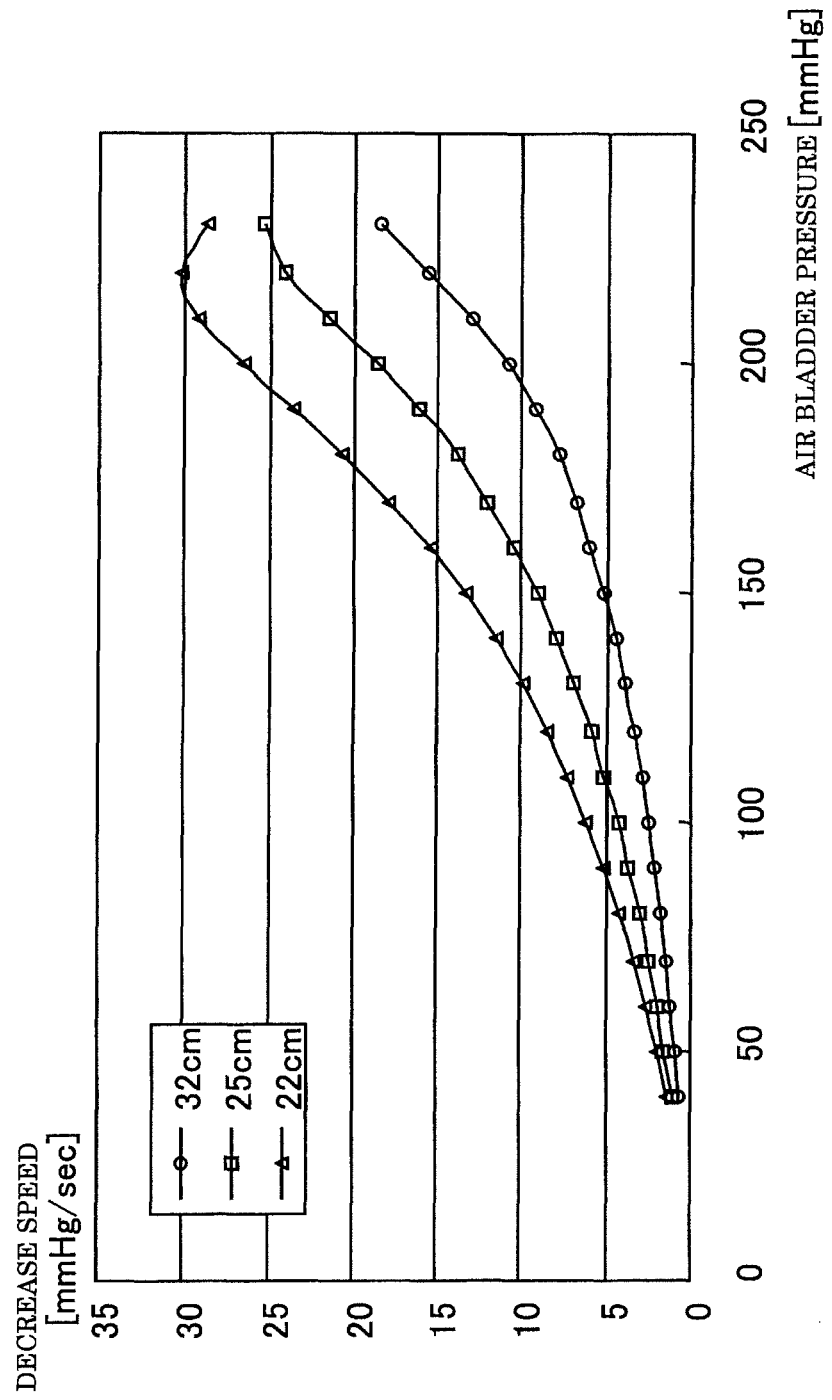
FIG. 6 is a diagram illustrating change rates in a decrease speed of a pressure in a measurement air bladder in the case where a driving voltage of a valve is held constant, for each of circumferential lengths of measurement areas.

Here, as shown in FIG. 6, a degree of change in the speed at which the pressure in an air bladder decreases differs depending on the circumferential length of the measurement area in the case where the driving voltage E1 is kept constant. Specifically, as shown in FIG. 6, the degree of change in the decrease speed increases as the circumferential length of the measurement area decreases, and the degree of change in the decrease speed decreases as the circumferential length of the measurement area increases. In other words, it can be said, based on the relationship illustrated in FIG. 6, that the circumferential length of the measurement area serves as a parameter for determining the driving voltage E1.

Accordingly, the driving voltage determination unit 412 determines the driving voltage E1 using the aforementioned relationship illustrated in FIG. 6. As a specific example, the driving voltage determination unit 412 stores the following formula (1) in advance, and determines the driving voltage E1 by substituting the obtained circumferential length information in that formula.

driving voltage $E1 = \alpha \times$ circumferential length information $+ \beta$           Formula (1)

Figure 7:
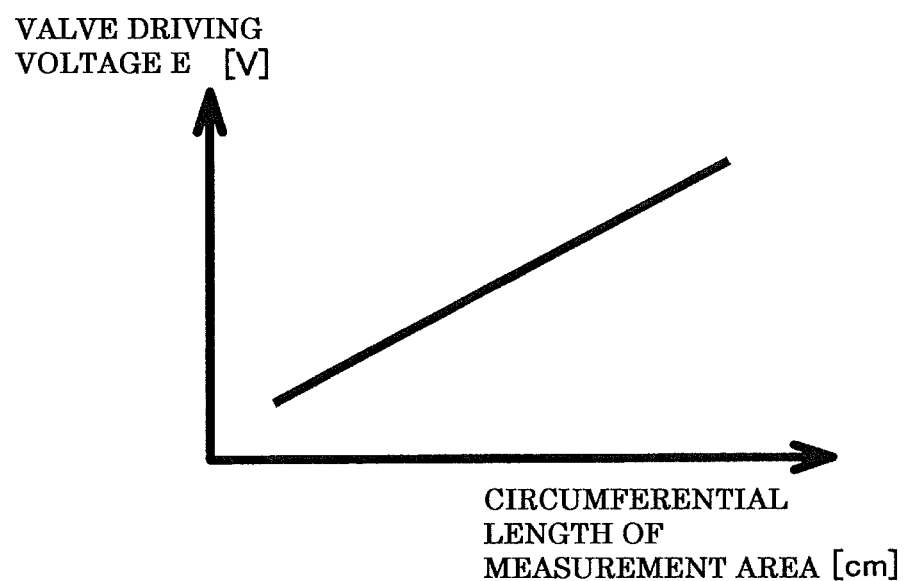
FIG. 7 is a diagram illustrating a relationship between a driving voltage and a circumferential length calculated using a relational expression between circumferential length information and a pump/valve driving voltage.

FIG. 7 is a diagram illustrating a relationship between the driving voltage E1 and the circumferential length calculated using the relational expression (1) between the circumferential length information and the driving voltage E1. By using the aforementioned formula (1), the driving voltage determination unit 412 determines a magnitude of the driving voltage E1 that is in proportion to the circumferential length of the measurement area, as shown in FIG. 7.

Figure 8:
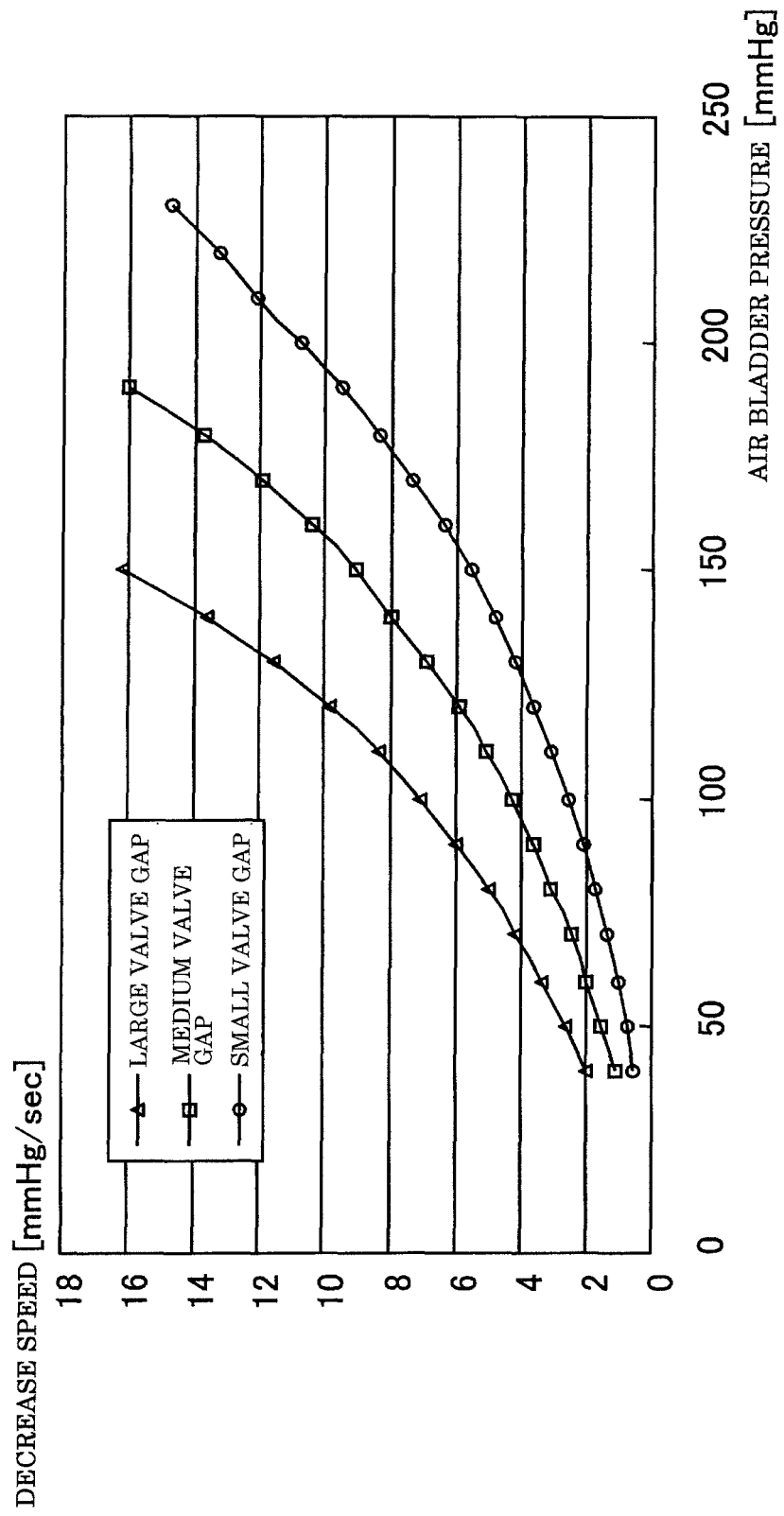
FIG. 8 is a diagram illustrating change rates in a decrease speed of a pressure in a measurement air bladder in the case where the circumferential length of the measurement area is the same.

FIG. 8 is a diagram illustrating change rates in the decrease speed of the pressure in the air bladder 13 in the case where the circumferential length of the measurement area is the same. As shown in FIG. 8, in the case where the circumferential length of the measurement area is the same, the rate of change in the speed at which the pressure in the air bladder 13 decreases differs depending on the gap in the valve 22, or in other words, depending on the magnitude of the driving voltage. Specifically, as shown in FIG. 8, the rate of change in a decrease speed increases as the gap in the valve 22 increases, and the rate of change in a decrease speed decreases as the gap decreases. According to one or more embodiments of the present invention, based on the relationship shown in FIG. 8, the gap is of a magnitude in which the decrease speed of the air bladder 13, from the calculation of a systolic blood pressure to the calculation of a diastolic blood pressure, is within a predetermined speed range.

To be more specific, according to one or more embodiments of the present invention, the gap is of a magnitude that results in a decrease speed in which the number of pressure pulse wave amplitude signals that can be detected during deflation between the systolic blood pressure and the diastolic blood pressure is greater than or equal to a predetermined number. According to one or more embodiments of the present invention, the aforementioned "predetermined number" is 5. The reason for this is that, as described in Japanese Patent No. 3,149,873 previously disclosed by the present applicants, it is acceptable, in consideration of the capabilities of an algorithm for measuring the decrease in pressure, to control the decrease speed so that approximately five pressure pulse wave amplitude signals are detected during deflation between the systolic blood pressure and the diastolic blood pressure.

Note that the magnitude of the gap in which five or more pressure pulse wave amplitude signals are measured during deflation between the systolic blood pressure and the diastolic blood pressure is obtained, for example, through experimentation or the like, and is assumed to be stored in advance in the driving voltage determination unit 412. According to one or more embodiments of the present invention, approximately 5 mmHg/sec to 20 mmHg/sec is a specific value thereof. Accordingly, the coefficients $\alpha$ and $\beta$ in the aforementioned formula (1) can be set to values that bring the blood pressure decrease speed in which the pressure of the air bladder 13 is within a range near the blood pressure value to within a decrease speed from approximately 5 mmHg/sec to 20 mmHg/sec. These coefficients $\alpha$ and $\beta$ are assumed to be found in advance through experimentation or the like and stored in the driving voltage determination unit 412. Although the driving voltage determination unit 412 takes the circumferential length information obtained through the stated formula (1) as an input and determines the driving voltage E1 in the above example, it should be noted that instead of formula (1), the driving voltage determination unit 412 may store a table that specifies the relationship between the circumferential length information and the driving voltage E1, and may read out the driving voltage E1 that corresponds to the obtained circumferential length information by referring to that table.

In the deflation operation of the aforementioned step S23, the CPU 40 determines the driving voltage E1 that corresponds to the circumferential length using the driving voltage determination unit 412, and outputs, to the driving circuit 27, a control signal for holding the determined driving voltage E1 and driving the valve 22.

Figure 9A:
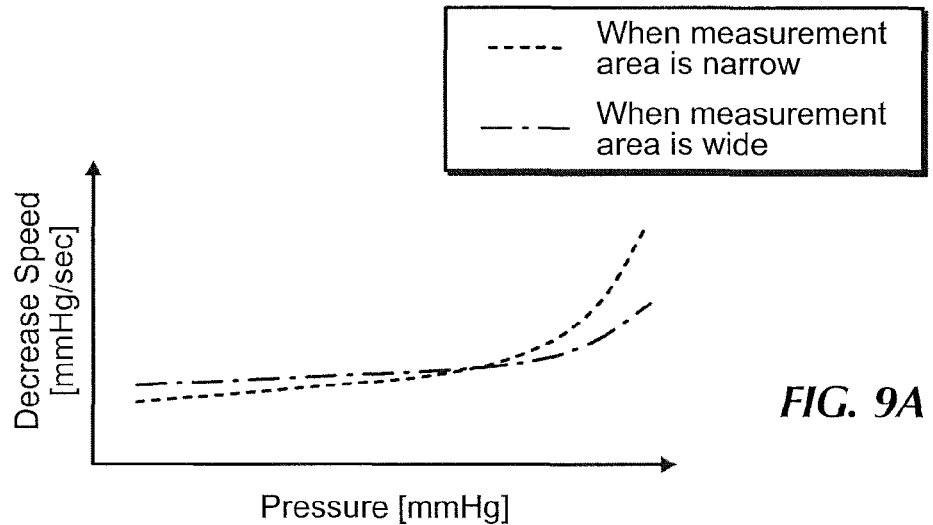
FIG. 9A is a diagram illustrating a relationship between a pressure in the measurement air bladder and the decrease speed in the sphygmomanometer according to the first embodiment.

As a result, during deflation, the speed at which the air bladder 13 deflates changes in accordance with pressure changes in the air bladder 13, as shown in FIG. 9A.

Figure 9B:
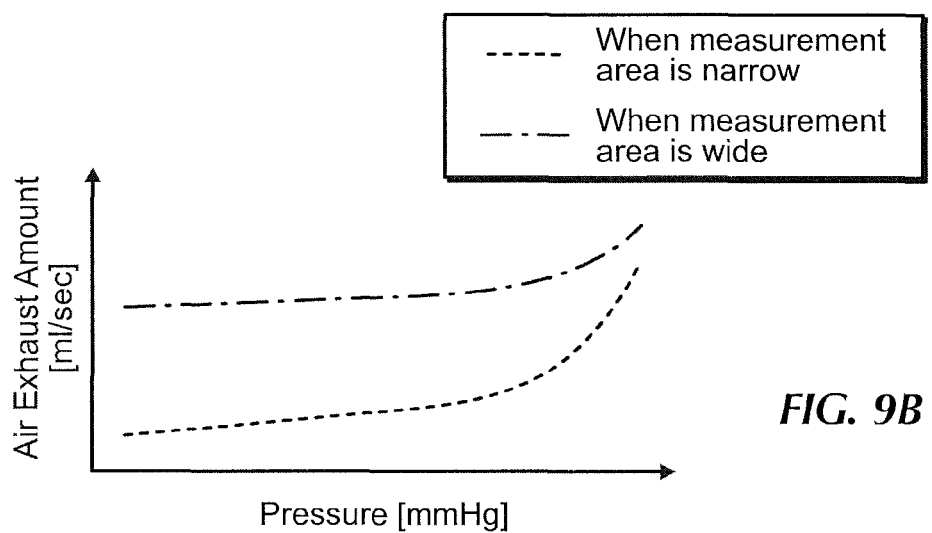
FIG. 9B is a diagram illustrating a relationship between a pressure in the measurement air bladder and an air exhaust amount in the sphygmomanometer according to the first embodiment.

In addition, during deflation, the exhaust amount from the valve 22 at the pressure in the air bladder 13 changes in accordance with pressure changes in the air bladder 13, as shown in FIG. 9B.

In other words, based on the relationships illustrated in FIGS. 9A and 9B, controlling the driving voltage E1 to be constant, or in other words, controlling the gap in the valve 22 to be constant, can be called a equivalent to controlling the driving voltage E1 so that the exhaust amount from the valve 22 and the speed at which the air bladder 13 deflates are in a proportional relationship.

Figure 9C:
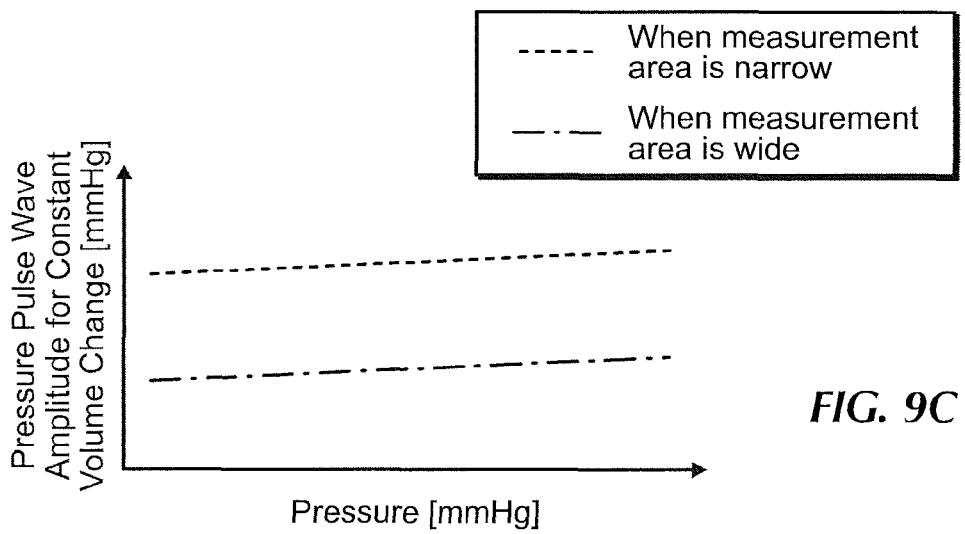
FIG. 9C is a diagram illustrating a relationship between a pressure in the measurement air bladder and a pressure pulse wave amplitude value for a set volume change in the sphygmomanometer according to the first embodiment.

By executing such feed-forward control, the CPU 40 can bring the flow amount of air from the air bladder 13 and the speed of deflation into a proportional relationship. Through this, it is possible to approach a constant detection accuracy for changes in the volume of the blood vessel, which in turn makes it possible to improve the measurement accuracy. In other words, as shown in FIG. 9C, a pressure pulse wave amplitude for a constant volume change can be made constant at a value that is based on the circumferential length of the measurement area, regardless of changes in the pressure within the air bladder 13.

Internal Pressure Control of Air Bladder 8

In the deflation operation of the aforementioned step S23, the CPU 40 controls the internal pressure of the air bladder 8 so that the internal pressure of the air bladder 8 and the internal pressure of the air bladder 13 are in a predetermined ratio.

Figure 10:
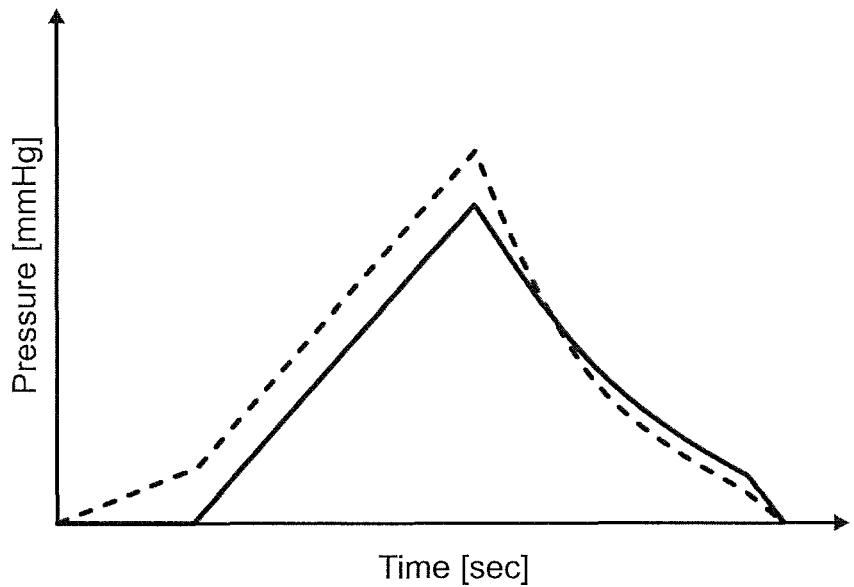
FIG. 10 is a diagram illustrating a relationship between internal pressure changes in a compressing air bladder and the measurement air bladder.
Figure 11:
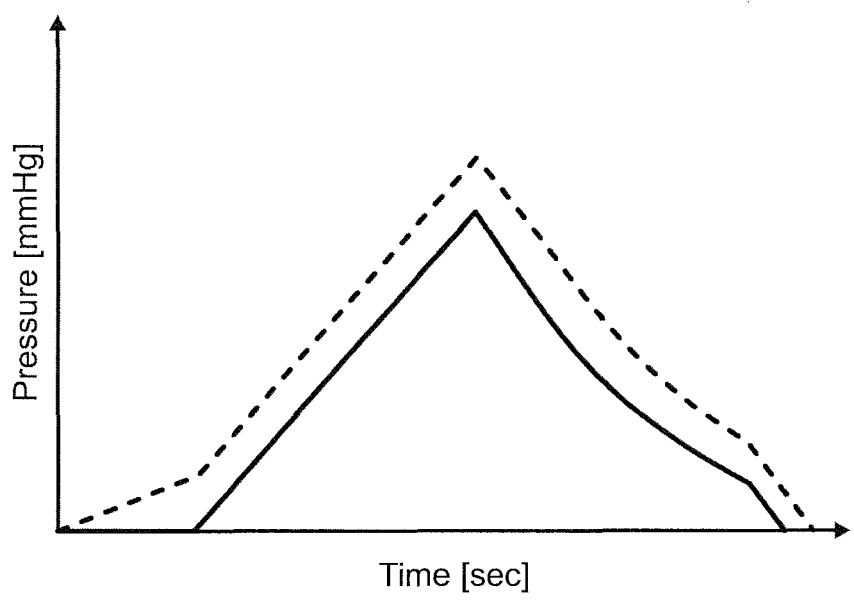
FIG. 11 is a diagram illustrating a relationship between internal pressure changes in the compressing air bladder and the measurement air bladder.

FIGS. 10 and 11 are diagrams illustrating relationships between a change in the internal pressure of the air bladder 8 and a change in the internal pressure of the air bladder 13; the solid lines indicate the internal pressure of the air bladder 13, whereas the dotted lines indicate the internal pressure of the air bladder 8.

As shown in FIG. 10, if the ratio between the internal pressure of the air bladder 8 and the internal pressure of the air bladder 13 changes during measurement (here, during deflation), there are cases where the shape of the curler 10 located between the air bladder 8 and the air bladder 13 is unstable and deforms. For example, as shown in FIG. 10, if the internal pressure of the air bladder 8 drops below the internal pressure of the air bladder 13, the strength at which the air bladder 8 compresses the curler 10 and the air bladder 13 will drop below the internal pressure of the air bladder 13. As a result, the curler 10 will be pressed outward due to the internal pressure of the air bladder 13, and vibrations resulting from that deformation can overlap with changes in the internal pressure of the air bladder 13 and be detected. This is referred to as a "false pulse wave", and leads to a worsening in the pulse measurement accuracy. This also causes a drop in the strength at which the air bladder 8 compresses the air bladder 13, which causes the wrapping of the air bladder 13 on the measurement area to become unstable. This, too, results in a worsening in the accuracy of the detected pulse wave.

Accordingly, as shown in FIG. 11, during measurement (here, during deflation), the CPU 40 changes the internal pressure of the air bladder 8 so that the ratio between the internal pressure of the air bladder 8 and the internal pressure of the air bladder 13 is greater than or equal to the predetermined ratio. Doing so stabilizes the curler 10 that is located between the two air bladders.

(1) Feedback Control

During the deflation operation of the aforementioned step S23, the second control unit 42 of the CPU 40 may monitor the internal pressure of the air bladder 13 and the internal pressure of the air bladder 8, and may carry out feedback control so that the predetermined ratio between the internal pressure of the air bladder 8 and the internal pressure of the air bladder 13 reaches a predetermined value.

In this case, as shown in FIG. 4, the second control unit 42 of the CPU 40 includes a driving voltage determination unit 422 for determining a voltage for driving the pump 31, the valve 32, and so on (called a "driving voltage E2" hereinafter).

The driving voltage determination unit 422 obtains the internal pressure of the air bladder 13 and the internal pressure of the air bladder 8 at a predetermined timing, and determines the driving voltage E2 so that the ratio between the internal pressure of the air bladder 8 and the internal pressure of the air bladder 13 becomes the predetermined ratio, specified in advance. A control signal for driving the valve 32 at the determined driving voltage E2 is generated, and the control signal is outputted to the driving circuit 37. Note that the aforementioned predetermined ratio is a value determined in advance through experimentation or the like, and is assumed to be stored in the second control unit 42 in advance.

At this time, even if the aforementioned feedback control is carried out by the first control unit 41, feed-forward control may also be carried out on the internal pressure of the air bladder 13.

Through this control, during deflation, the internal pressure of the air bladder 8 can be changed so that the ratio between the internal pressure of the air bladder 8 and the internal pressure of the air bladder 13 becomes the predetermined ratio. As a result, the curler 10 located between the air bladder 13 and the air bladder 8 can be prevented from deforming during measurement (during deflation), which in turn makes it possible to improve the measurement accuracy.

(2) Feed-Forward Control

Alternatively, in the case where the first control unit 41 is performing the stated feed-forward control in the aforementioned step S23, the second control unit 42 of the CPU 40 may carry out feed-forward control that controls the internal pressure of the air bladder 8 by outputting a control signal based on a pre-set control signal outputted by the first control unit 41.

In this case, as shown in FIG. 4, the second control unit 42 of the CPU 40 includes the driving voltage determination unit 422 for determining the driving voltage E2 for driving the pump 31, the valve 32, and so on.

The driving voltage determination unit 422 obtains the driving voltage E1 determined as described above by obtaining the control signal outputted from the first control unit 41. Then, the driving voltage E2 is calculated so that the internal pressure of the air bladder 8 becomes a value that achieves the predetermined ratio relative to the internal pressure of the air bladder 13 that is undergoing the stated control; the determined driving voltage E2 is then outputted to the driving circuits 36 and 37. Note that the aforementioned predetermined ratio is a value determined in advance through experimentation or the like, and is assumed to be stored in the second control unit 42 in advance.

Through this, when, during deflation, the internal pressure of the air bladder 13 is changed as a result of the feed-forward control so that the flow amount of air from the air bladder 13 and the deflation speed approach a proportional relationship, the internal pressure of the air bladder 8 can be changed so that the ratio between the internal pressure of the air bladder 8 and the internal pressure of the air bladder 13 becomes the predetermined ratio. As a result, the curler 10 located between the air bladder 13 and the air bladder 8 can be prevented from deforming during measurement (during deflation), which in turn makes it possible to improve the measurement accuracy.

(3) Ratio of Internal Pressures of Air Bladder 13 and Air Bladder 8 During Feed-Forward Control The above example assumes that the ratio of the internal pressures of the air bladder 13 and the air bladder 8 during deflation is a predetermined ratio determined in advance through experimentation or the like, and that the ratio is stored in advance in the second control unit 42.

However, the driving voltage determination unit 422 may carry out calculations based on predetermined input values, and may store correspondence relationships between input values and the stated predetermined ratio in advance and specify the predetermined ratio based on an input value. The circumferential length of the measurement area, the blood pressure value of the user, the cuff size, and the maximum inflation value of the air bladder 13 can be given as examples of input values. Examples of each of these input values will be described below.

When Using Ratio Based on Circumferential Length of Measurement Area

In this case, as shown in FIG. 4, the second control unit 42 includes an obtainment unit 421 for obtaining the circumferential length information, which is information indicating the circumferential length of the measurement area of the user.

The obtainment unit 421 obtains the circumferential length of the measurement area in the same manner as the circumferential length information obtainment unit 411. In other words, when circumferential length information indicating, for example, "wide", "narrow", or the like is inputted during measurement using, for example, a switch of which the operating unit 3 is partially configured, the obtainment unit 421 obtains the circumferential length information based on an operation signal from the operating unit 3. Alternatively, the circumferential length information may be obtained through an input from the external I/F 80.

Further still, internal pressure control for obtaining the circumferential length information may be carried out by the CPU 40, and the obtainment unit 421 may obtain the circumferential length information based on the result of that control. The internal pressure control for obtaining the circumferential length information may be the same as the control for obtaining the circumferential length information using the circumferential length information obtainment unit 411.

Figure 12:
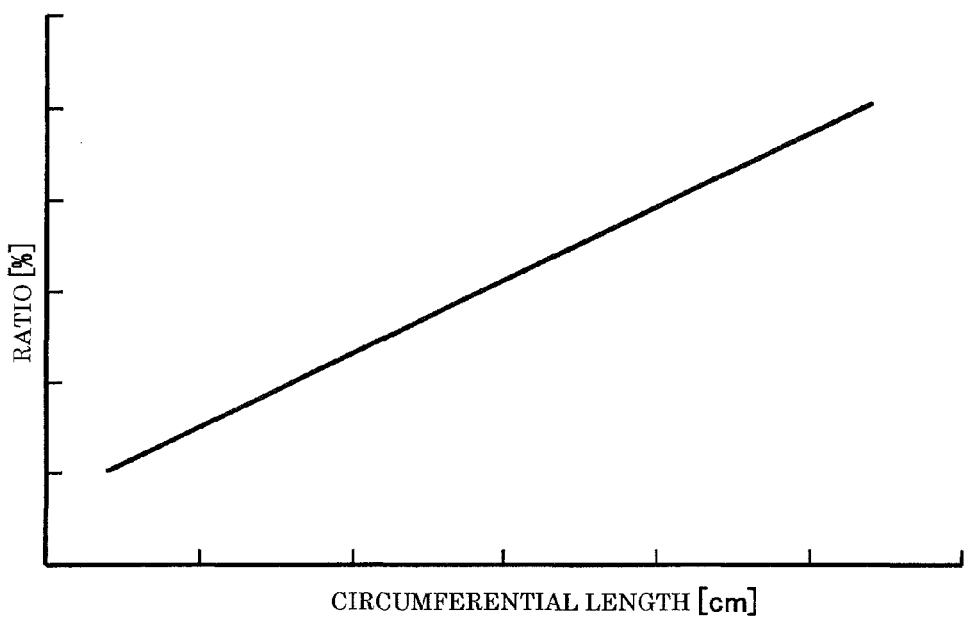
FIG. 12 is a diagram illustrating a specific example of a relationship between an upper arm circumference serving as a specific example of a circumferential length, and a predetermined ratio indicating a ratio of internal pressures of the measurement air bladder and the compressing air bladder.
Figure 13:
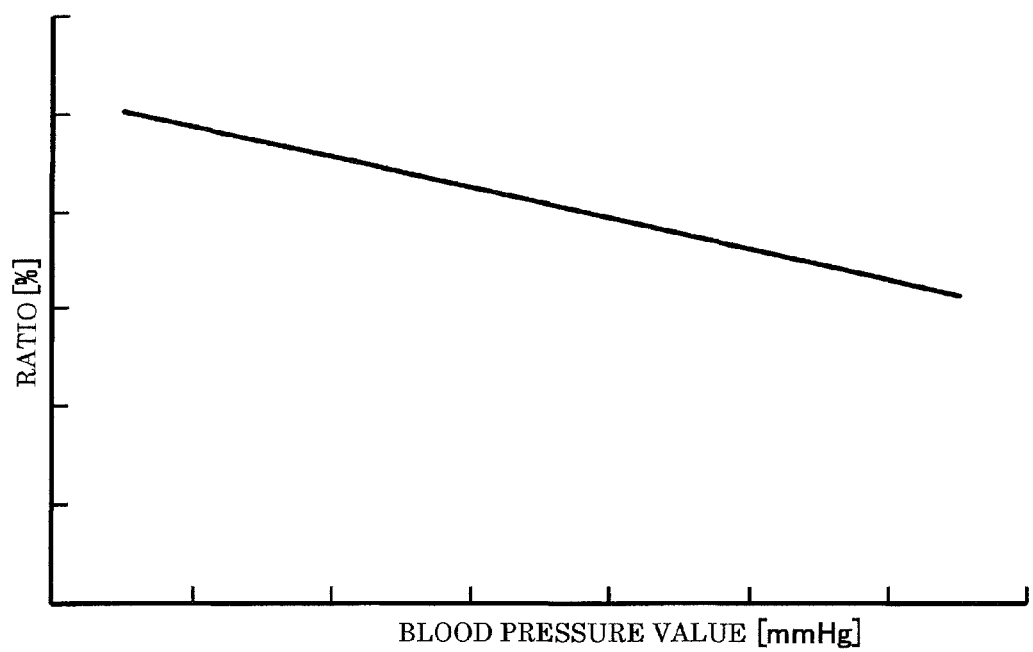
FIG. 13 is a diagram illustrating a specific example of a relationship between a maximum inflation value of the measurement air bladder and the predetermined ratio indicating a ratio of the internal pressures of the measurement air bladder and the compressing air bladder.

The driving voltage determination unit 422 stores, in advance, a correspondence relationship or relational expression between the circumferential length and the ratio of the internal pressure of the air bladder 8 to the internal pressure of the air bladder 13. FIG. 12 is a diagram illustrating a specific example of a relationship between an upper arm circumference serving as a specific example of the circumferential length, and the predetermined ratio indicating the ratio of internal pressures of the air bladder 13 and the air bladder 8. Specifically, as shown in FIG. 12, the driving voltage determination unit 422 stores a correspondence relationship or relational expression in which the ratio of the internal pressure of the air bladder 8 to the internal pressure of the air bladder 13 increases as the circumferential length of the measurement area increases.

The driving voltage determination unit 422 refers to the stored correspondence relationship, specifies the ratio corresponding to the circumferential length of the measurement area of the user obtained by the obtainment unit 421, and determines the driving voltage E2 so that the ratio of the internal pressure of the air bladder 8 to the internal pressure of the air bladder 13 becomes the stated ratio. Alternatively, the driving voltage E2 is calculated by substituting the obtained circumferential length of the measurement area of the user in the stated relational expression. A control signal is then generated and outputted.

Through this, control is carried out so that the ratio of the internal pressure of the air bladder 8 to the internal pressure of the air bladder 13 becomes a ratio that is based on the circumferential length of the measurement area of the user.

When Using Ratio Based on Blood Pressure Value of User

In this case, as shown in FIG. 4, the second control unit 42 includes the obtainment unit 421 for obtaining a blood pressure value of the user.

In the case where measurement operations that calculate the blood pressure value during the deflation process are carried out as in this example, the obtainment unit 421 can obtain an estimated value for the blood pressure value during the inflation process of the air bladder 13 as the blood pressure value of the user. In other words, in this case, the calculation unit 43 calculates the blood pressure value of the user based on changes in the internal pressure of the air bladder 13 during the inflation process, and inputs that value to the second control unit 42 as the estimated value.

Alternatively, in the case where a blood pressure value is stored in the memory 7 as a measurement result for that user, the obtainment unit 421 may obtain the blood pressure value of the user by reading out that blood pressure value from a predetermined region in the memory 7. Note that in this case, the latest blood pressure value may be read out, or the average value of blood pressure values in a predetermined range may be used.

Note also that the blood pressure value referred to here may be a systolic blood pressure value, a diastolic blood pressure value, or an average blood pressure value that is an average value thereof. It is assumed that the systolic blood pressure value is used in the following example.

The driving voltage determination unit 422 stores, in advance, a correspondence relationship or relational expression between the blood pressure value and the ratio of the internal pressure of the air bladder 8 to the internal pressure of the air bladder 13. Specifically, the driving voltage determination unit 422 stores a correspondence relationship or relational expression in which the ratio of the internal pressure of the air bladder 8 to the internal pressure of the air bladder 13 decreases as the systolic blood pressure value of the user increases.

The driving voltage determination unit 422 refers to the stored correspondence relationship, specifies the ratio corresponding to the blood pressure value of the user obtained by the obtainment unit 421, and determines the driving voltage E2 so that the ratio of the internal pressure of the air bladder 8 to the internal pressure of the air bladder 13 becomes the stated ratio. Alternatively, the driving voltage E2 is calculated by substituting the obtained blood pressure value of the user in the stated relational expression. A control signal is then generated and outputted.

Through this, control is carried out so that the ratio of the internal pressure of the air bladder 8 to the internal pressure of the air bladder 13 becomes a ratio that is based on the blood pressure value of the user.

When Using Ratio Based on Cuff Size

In the case where the cuff size is variable, the second control unit 42 may, as shown in FIG. 4, include the obtainment unit 421 for obtaining size information, which is information indicating the cuff size, in order to establish a ratio based on the cuff size.

Here, the cuff size corresponds to the size of the volumes of the air bladders 13 and 8; the volumes of air bladders 13 and 8 are large in the case where the cuff size is large, whereas the volumes of the air bladders 13 and 8 are small in the case where the cuff size is small. A case in which the cuff size is variable corresponds to a case in which, for example, the body compression/stabilizing unit contained in the inner circumferential area of the housing 60 or the housing 60 itself can be removed from the main body 2 and replaced, and a body compression/stabilizing unit, the housing 60 that includes that unit, and so on that are based on the cuff size is connected to the main body 2 and used.

For example, when a cuff size such as "large", "medium", or "small" is inputted during measurement using a switch or the like of which the operating unit 3 is partially configured, the obtainment unit 421 obtains the cuff size from an operation signal from the operating unit 3. Alternatively, the cuff size may be obtained through input from the external I/F 80. Further still, in the case where a sensor or the like that detects the type of body compression/stabilizing unit or housing 60 that is connected to a connection portion between the body compression/stabilizing unit or the housing 60 and the main body 2 is provided, the obtainment unit 421 may determine the cuff size based on a signal outputted from that sensor.

The driving voltage determination unit 422 stores, in advance, a correspondence relationship or relational expression between the cuff size and the ratio of the internal pressure of the air bladder 8 to the internal pressure of the air bladder 13. Specifically, the driving voltage determination unit 422 stores a correspondence relationship or relational expression in which the ratio of the internal pressure of the air bladder 8 to the internal pressure of the air bladder 13 increases as the cuff size increases.

The driving voltage determination unit 422 refers to the stored correspondence relationship, specifies the ratio corresponding to the cuff size obtained by the obtainment unit 421, and determines the driving voltage E2 so that the ratio of the internal pressure of the air bladder 8 to the internal pressure of the air bladder 13 becomes the stated ratio. Alternatively, the driving voltage E2 is calculated by substituting the obtained cuff size in the stated relational expression. A control signal is then generated and outputted.

Through this, control is carried out so that the ratio of the internal pressure of the air bladder 8 to the internal pressure of the air bladder 13 becomes a ratio that is based on the cuff size.

When Using Ratio Based on Maximum Inflation Value of Air Bladder 13

In this case, as shown in FIG. 4, the second control unit 42 includes the obtainment unit 421 for obtaining a maximum inflation value of the air bladder 13. The "maximum inflation value of the air bladder 13" referred to here indicates a maximum value for the internal pressure of the air bladder 13 during the inflation process, and the obtainment unit 421 obtains the maximum inflation value of the air bladder 13 by monitoring the internal pressure of the air bladder 13 detected by the pressure sensor 23 during the inflation process.

Alternatively, the obtainment unit 421 may calculate the maximum inflation value from the blood pressure value of the user. In this case, as mentioned above, the obtainment unit 421 obtains the blood pressure value of the user.

The driving voltage determination unit 422 stores, in advance, a correspondence relationship or relational expression between the maximum inflation value of the air bladder 13 and the ratio of the internal pressure of the air bladder 8 to the internal pressure of the air bladder 13. Specifically, the driving voltage determination unit 422 stores a correspondence relationship or relational expression in which the ratio of the internal pressure of the air bladder 8 to the internal pressure of the air bladder 13 decreases as the maximum inflation value of the air bladder 13 increases.

The driving voltage determination unit 422 refers to the stored correspondence relationship, specifies the ratio corresponding to the maximum inflation value of the air bladder 13 obtained by the obtainment unit 421, and determines the driving voltage E2 so that the ratio of the internal pressure of the air bladder 8 to the internal pressure of the air bladder 13 becomes the stated ratio. Alternatively, the driving voltage E2 is calculated by substituting the obtained maximum inflation value in the stated relational expression. A control signal is then generated and outputted.

Through this, control is carried out so that the ratio of the internal pressure of the air bladder 8 to the internal pressure of the air bladder 13 becomes a ratio that is based on the maximum inflation value of the air bladder 13.

When Using a Combination of the Above

The above examples are examples in which the driving voltage determination unit 422 specifies the ratio of the internal pressure of the air bladder 8 to the internal pressure of the air bladder 13 using one of the circumferential length of the measurement area, the blood pressure value of the user, the cuff size, and the maximum inflation value of the air bladder 13 as the input value. However, embodiments of the present invention are not limited to only one of the aforementioned examples, and the predetermined ratio may be specified using a combination of two or more of those examples.

For example, the driving voltage determination unit 422 may specify a ratio based on the circumferential length and blood pressure value of the user as input values. In this case, the obtainment unit 421 obtains the circumferential length and blood pressure value of the user.

Figures 14, 15:
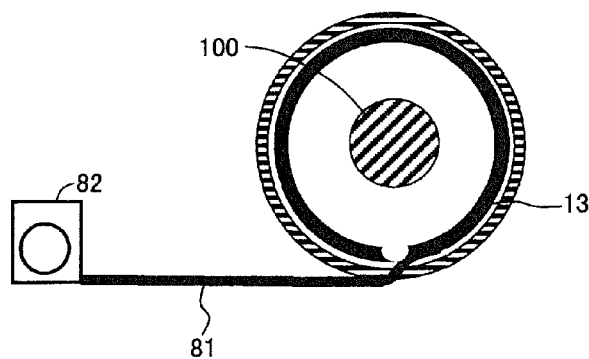
FIG. 14 is a diagram illustrating a specific example of a relationship between an upper arm circumference, a systolic blood pressure value, and a predetermined ratio indicating a ratio of the internal pressures of the measurement air bladder and the compressing air bladder.
FIG. 15 is a diagram illustrating an outline of a sphygmomanometer according to a second embodiment.

The driving voltage determination unit 422 stores, in advance, a correspondence relationship or relational expression between the circumferential length and blood pressure value of the user and the ratio of the internal pressure of the air bladder 8 to the internal pressure of the air bladder 13. FIG. 14 is a diagram illustrating a specific example of a relationship between an upper arm circumference serving as a specific example of the circumferential length, the systolic blood pressure value serving as a specific example of the blood pressure value, and the predetermined ratio indicating the ratio of internal pressures of the air bladder 13 and the air bladder 8. A relational expression such as Ratio=α×upper arm circumference+β×SBP (where α and β are coefficients and SBP is the systolic blood pressure value) can be given as the relational expression. In this specific case, as shown in FIG. 14, the driving voltage determination unit 422 stores a correspondence relationship or relational expression in which the ratio of the internal pressure of the air bladder 8 to the internal pressure of the air bladder 13 increases as the circumferential length of the measurement area increases, and the ratio of the internal pressure of the air bladder 8 to the internal pressure of the air bladder 13 decreases as the systolic blood pressure value increases.

The driving voltage determination unit 422 refers to the stored correspondence relationship, specifies the ratio corresponding to the circumferential length and blood pressure value of the user obtained by the obtainment unit 421, and determines the driving voltage E2 so that the ratio of the internal pressure of the air bladder 8 to the internal pressure of the air bladder 13 becomes the stated ratio. Alternatively, the driving voltage E2 is calculated by substituting the obtained circumferential length and blood pressure value of the user in the stated relational expression. A control signal is then generated and outputted.

Through this, control is carried out so that the ratio of the internal pressure of the air bladder 8 to the internal pressure of the air bladder 13 becomes a ratio that is based on the circumferential length and blood pressure value of the user.

By the second control unit 42 determining the ratio of the internal pressures of the air bladder 13 and the air bladder 8 in this manner during feed-forward control, the ratio of the internal pressure of the air bladder 8 to the internal pressure of the air bladder 13 can be set to the optimal ratio for the user, the circumstances at the time of measurement, and so on. This makes it possible to keep the strength at which the air bladder 8 compresses the air bladder 13 at the optimal level during measurement (during deflation), which in turn makes it possible to improve the measurement accuracy.

(4) Control of Ratio of Internal Pressures of Air Bladder 13 and Air Bladder 8 During Feed-Forward Control In the above example, the second control unit 42 determines the ratio of the internal pressures of the air bladder 13 and the air bladder 8 at a predetermined timing during deflation, such as at the start of deflation, and outputs a control signal so that the ratio determined at that timing is maintained thereafter.

However, the second control unit 42 may change the determined ratio at a predetermined timing. A measured internal pressure of the air bladder 13 (or a pulse wave amplitude obtained from an internal pressure), a strength of compression by the air bladder 8, and an amount of time elapsed from the start of deflation can be given as examples of the predetermined timing.

In this case, as shown in FIG. 4, the second control unit 42 includes the obtainment unit 421 for obtaining the measured internal pressure of the air bladder 13 (or a pulse wave amplitude obtained from an internal pressure), the strength of compression by the air bladder 8, or the amount of time elapsed from the start of deflation.

The driving voltage determination unit 422 stores, in advance, the stated predetermined ratio for each measured internal pressure of the air bladder 13 (or pulse wave amplitude obtained from an internal pressure), strength of compression by the air bladder 8, or amount of time elapsed from the start of deflation. It is then determined, at predetermined intervals, whether or not the measured internal pressure of the air bladder 13 (or pulse wave amplitude obtained from an internal pressure), strength of compression by the air bladder 8, or amount of time elapsed from the start of deflation has reached the stored timing for making the change. In the case where it has been determined that the timing for making the change has been reached, the driving voltage determination unit 422 reads out the ratio based on that timing, determines the driving voltage E2 so that the ratio of the internal pressure of the air bladder 8 to the internal pressure of the air bladder 13 is that ratio, and generates and outputs a control signal.

Alternatively, the second control unit 42 may change the stated predetermined ratio using, as the predetermined timing, a timing at which the rate of change in the internal pressure of the air bladder 13 in a pressure segment, when the internal pressure of the air bladder 13 is between predetermined pressures P1 and P2, has reached a predetermined rate of change. For example, a pressure segment between the maximum inflation value of the air bladder 13 and (maximum inflation value−50 mmHg) can be given as an example of the stated pressure segment.

Furthermore, the stated predetermined ratio may be changed based on a timing determined based on a combination of two or more of the conditions of the measured internal pressure of the air bladder 13, the strength of compression by the air bladder 8, and an amount of time that has elapsed from the start of deflation, in the same manner as when determining the ratio between the internal pressure of the air bladder 13 and the internal pressure of the air bladder 8. For example, the driving voltage determination unit 422 may store, in advance, a relationship between the predetermined ratio and the internal pressure of the air bladder 13 and strength of compression by the air bladder 8, and may change the stated predetermined ratio to the ratio specified in accordance with the combination of the predetermined ratio and the internal pressure of the air bladder 13 and strength of compression by the air bladder 8 at the timing at which those conditions have been met.

Through this, the relationship between the internal pressures of the air bladder 13 and the air bladder 8 can be properly maintained as the measurement progresses, which makes it possible to improve the measurement accuracy.

Second Embodiment

With the sphygmomanometer 1 according to the first embodiment, the air bladder 8 is employed as a member for compressing the air bladder 13 on the measurement area over the curler 10.

However, the configuration for compressing the air bladder 13 on the measurement area is not limited to an air bladder over the curler 10, and another compression mechanism may be employed. As another such example, FIG. 15 illustrates an overview of a sphygmomanometer 1' according to a second embodiment.

As shown in FIG. 15, the sphygmomanometer 1' according to the second embodiment includes a wire 81 for pressing the air bladder 13 against the measurement area instead of the air bladder 8 and curler 10 of the sphygmomanometer 1, and a wire take-up unit 82 serving as a mechanism for taking up the wire 81 instead of the pump 31 and valve 32. One end of the air bladder 13 is anchored to the cuff, and the other end is connected to the stated wire. Alternatively, the configuration may be such that the stated wire is connected to both ends of the air bladder 13.

Figure 16:
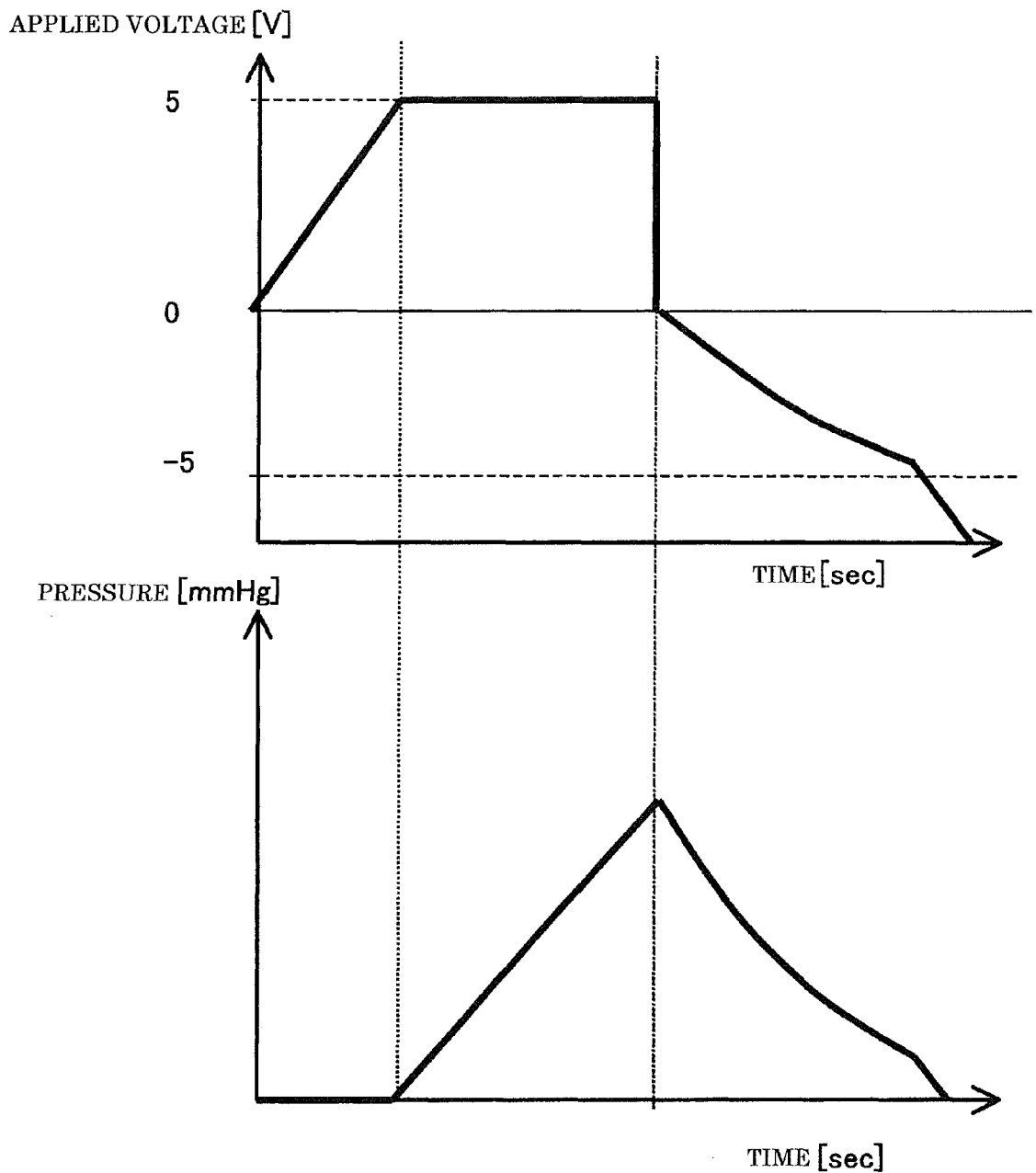
FIG. 16 is a diagram illustrating the correspondence between a change in a driving voltage for driving a wire take-up unit, and a change in the internal pressure of a measurement air bladder that is compressed via a wire in order to compress a measurement area.

A driving circuit (not shown) that corresponds to the driving circuits 36 and 37 is connected to the CPU 40, and drives the wire take-up unit 82 in accordance with a control signal from the CPU 40. FIG. 16 is a diagram illustrating a correspondence between changes in a voltage applied to the driving circuit of the wire take-up unit 82 for driving the wire take-up unit 82 (a driving voltage E3) and changes in the internal pressure of the air bladder 13 that is compressed on the measurement area by the wire 81; the upper section of the diagram indicates changes in the driving voltage E3, whereas the lower section of the diagram indicates changes in the internal pressure of the air bladder 13. As shown in FIG. 16, here, the changes in the driving voltage E3 and the changes in the internal pressure of the air bladder 13 generally correspond to each other. In this manner, the strength at which the wire 81 compresses the air bladder 13 is controlled by controlling the driving voltage E3.

The other configurations of the sphygmomanometer 1' are generally the same as the configurations of the sphygmomanometer 1. In other words, the CPU 40 includes the first control unit 41, and feedback control or feed-forward control is carried out by the first control unit 41 on the internal pressure of the air bladder 13 during deflation.

The CPU 40 also includes the second control unit 42, and the second control unit 42 may carry out feedback control on the internal pressure of the air bladder 8 during deflation, or feed-forward control may be carried out in the case where feed-forward control is carried on the internal pressure of the air bladder 13.

The specific details of these controls are generally the same as those in the sphygmomanometer 1. However, with the sphygmomanometer 1', the second control unit 42 controls the wire take-up unit 82 instead of controlling the pump 31 and the valve 32. Accordingly, the driving voltage determination unit 422 of the second control unit 42 determines the driving voltage E3 in the same manner as the aforementioned driving voltage E2, and outputs a control signal.

In this manner, even if the member for compressing the air bladder 13 on the measurement area has a configuration aside from the air bladder 8 and the curler 10, the second control unit 42 outputs a control signal to the mechanism that adjusts the compression strength in the same manner as the method described in the first embodiment; this makes it possible to prevent deformation in the curler 10 located between the air bladder 13 and the compression member during measurement (during deflation), which in turn makes it possible to improve the measurement accuracy.

Note that the above example describes the CPU 40 as calculating the blood pressure value based on changes in the internal pressure of the air bladder 13 as the air bladder 13 deflates. However, as another example, the CPU 40 may calculate the blood pressure value based on changes in the internal pressure of the air bladder 13 as the air bladder 13 inflates. In this case, replacing "during deflation" with "during inflation" in the aforementioned descriptions of the internal pressure control makes it possible to control the internal pressure during measurement in the same manner. Accordingly, in the same manner as described above, the curler 10 located between the air bladder 13 and the compression member can be prevented from deforming during measurement (during inflation), which in turn makes it possible to improve the measurement accuracy.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1, 1' sphygmomanometer
2 main body
3 operating unit
4 display unit
5 measurement section
6, 7 memory
13, 8 air bladder
10 curler
20, 30 air system
21, 31 pump
22, 32 valve
23, 33 pressure sensor
26, 27, 36, 37 driving circuit
28, 38 oscillation circuit
41 first control unit
42 second control unit
43 calculation unit
44 display control unit
60 housing
70 cover
80 external I/F
81 wire
82 wire take-up unit
100 upper arm
411 circumferential length information obtainment unit
412, 422 driving voltage determination unit
421 obtainment unit
E1, E2, E3 driving voltage

The invention claimed is:
1. An electronic sphygmomanometer comprising:
a first fluid bladder;
a first adjustment unit that injects/exhausts a fluid into/from said first fluid bladder at a variable speed;
a sensor that detects an internal pressure of said first fluid bladder;
a wrapping unit for wrapping said first fluid bladder around a measurement area of a measurement subject at a variable wrapping strength;
a second adjustment unit that adjusts the wrapping strength of said wrapping unit; and
a control unit,
wherein said control unit executes:
a first control process that outputs a first control signal to said first adjustment unit so that a rate of change in the internal pressure and/or fluid amount in said first fluid bladder becomes a predetermined rate of change;

a second control process that outputs a second control signal to said second adjustment unit so that said wrapping strength reaches a predetermined ratio with the rate of change in the internal pressure and/or fluid amount in said first fluid bladder under said first control process; and a calculation process that calculates a blood pressure value of said measurement subject based on a change in the internal pressure of said first fluid bladder detected under said first control process.

2. The electronic sphygmomanometer according to claim 1, wherein said first control signal is set in advance so that the rate of change in the internal pressure in said first fluid bladder and the rate of change in the fluid amount in said first fluid bladder are in a proportional relationship, wherein said second control signal is set in advance in according with said first control signal so as to achieve said predetermined ratio, and wherein said control unit carries out feed-forward control on said first control process and said second control process.

3. The electronic sphygmomanometer according to claim 1, wherein said wrapping unit comprises a second fluid bladder that is located further from the measurement area than said first fluid bladder when worn on the measurement area, wherein said second adjustment unit comprises a pump for injecting and/or a value for exhausting the fluid into/from said second fluid bladder at a variable speed, and wherein said second control process comprises a process for determining a driving voltage for said pump and/or said valve.

4. The electronic sphygmomanometer according to claim 1, wherein said control unit sets said predetermined ratio to a pre-set ratio or changes said predetermined ratio using a pre-set compensation formula in accordance with at least one of: a circumferential length of the measurement area, an already-measured blood pressure value of said measurement subject, a blood pressure value of said measurement subject estimated during inflation, a size of said first fluid bladder, and a maximum value of the pressure in said first fluid bladder.

5. The electronic sphygmomanometer according to claim 4, wherein said control unit determines the circumferential length of said measurement area and/or the size of said first fluid bladder based on the rate of change in the internal pressure of said first fluid bladder during inflation.

6. The electronic sphygmomanometer according to claim 4, wherein said control unit determines the blood pressure value of said measurement subject by obtaining a previous measurement result.

7. The electronic sphygmomanometer according to claim 4, wherein in said calculation process, said control unit calculates said blood pressure value based on a change in the internal pressure in said first fluid bladder when said first fluid bladder is deflating under said first control process, and wherein said control unit takes the blood pressure value calculated based on a change in the internal pressure in said first fluid bladder when said first fluid bladder is inflating as a blood pressure value of said measurement subject used to determine said predetermined ratio.

8. The electronic sphygmomanometer according to claim 4, further comprising:

an input unit that accepts an input of said at least one of a circumferential length of said measurement area, said already-measured blood pressure value of said measurement subject, a size of said first fluid bladder, and a maximum value of the pressure in said first fluid bladder.

9. The electronic sphygmomanometer according to claim 4, further comprising:

a readout unit that reads out, from another device, said at least one of a circumferential length of said measurement area, said already-measured blood pressure value of said measurement subject, a size of said first fluid bladder, and a maximum value of the pressure in said first fluid bladder.

10. The electronic sphygmomanometer according to claim 1, wherein said control unit changes said predetermined ratio to a pre-set ratio or changes said predetermined ratio using a pre-set compensation formula at at least one of a time when the internal pressure of said first fluid bladder reaches a predetermined level, a time when said wrapping strength reaches a predetermined level, and a time when a predetermined amount of time has elapsed following a predetermined point in time of a measurement process.

11. The electronic sphygmomanometer according to claim 1, wherein said control unit changes said predetermined ratio to a pre-set ratio or changes said predetermined ratio using a pre-set compensation formula in accordance with a size of a pulse wave amplitude detected from the internal pressure of said first fluid bladder.

12. A control method for an electronic sphygmomanometer, said electronic sphygmomanometer comprising a first fluid bladder, a first adjustment unit that injects/exhausts a fluid into/from said first fluid bladder at a variable speed, a sensor that detects an internal pressure of said first fluid bladder, and a wrapping unit for wrapping said first fluid bladder around a measurement area of a measurement subject at a variable wrapping strength, and said control method comprising:

a step of controlling said first adjustment unit so that a rate of change in the internal pressure and/or fluid amount in said first fluid bladder becomes a predetermined rate of change;

a step of controlling a second adjustment unit so that said wrapping strength reaches a predetermined ratio with the rate of change in the internal pressure and/or fluid amount in said first fluid bladder under the control in the step of controlling said first adjustment unit; and a step of calculating a blood pressure value of said measurement subject based on a change in the internal pressure of said first fluid bladder detected under the control in the step of controlling said first adjustment unit.

* * * * *